United States Patent [19]

Maki et al.

[11] 4,358,461
[45] Nov. 9, 1982

[54] ANTIALLERGIC AGENT

[75] Inventors: Yoshitaka Maki, Kyoto; Shinji Terao, Toyonaka; Masazumi Watanabe, Kawanishi, all of Japan

[73] Assignee: Takeda Chemical Industries, Ltd., Osaka, Japan

[21] Appl. No.: 250,298

[22] Filed: Apr. 2, 1981

[30] Foreign Application Priority Data

Apr. 21, 1980 [JP] Japan ................................. 55-53127

[51] Int. Cl.$^3$ .............................................. A61K 31/12
[52] U.S. Cl. ................................................... 424/331
[58] Field of Search ......................................... 424/331

[56] References Cited

U.S. PATENT DOCUMENTS 3,894,153  7/1975  Yamamoto ......................... 424/331
3,957,836  5/1976  Morimoto et al. .............. 260/396 R

OTHER PUBLICATIONS

Handbook of Nonprescription Drugs—6th Ed., 1979, pp. 115–123.

Primary Examiner—Leonard Schenkman
Attorney, Agent, or Firm—Wenderoth, Lind & Ponack

[57] ABSTRACT

A mammal suffering from allergic disease due to SRS-A, such as skin symptoms, asthma, rhinitis, etc. is treated by administering to said mammal an effective amount of a compound of the formula:

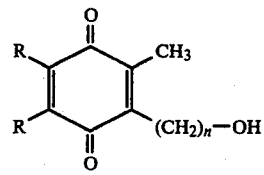

wherein R is methoxy or methyl, or two R's taken together represent —CH=CH—CH=CH—; and n is an integer of 4 to 22.

7 Claims, No Drawings

ANTIALLERGIC AGENT

This invention relates to a new antiallergic agent.

Diseases caused by hypersensitivity reactions are generally classified into immediate and delayed types of allergy, and the mechanism proposed as underlying the former type of hypersensitivity reaction is such that an antigen-antibody interaction generates and releases a chemical mediator at the local site of the body, and this mediator contracts the bronchial, pulmonary vein and other smooth muscles, increases the vascular permeability of the skin or otherwise does harm to the body. The mediator may for example be histamine or the lipoxygenase-catalyzed metabolites of poly-unsaturated fatty acids (especially arachidonic acid), such as slow reacting substance of anaphylaxis (hereafter briefly, SRS-A). Compounds effective against allergic diseases related to SRS-A are still now under exploratory investigation and all that have been reported, within the best of our knowledge, are 3-amino-1-[m-(trifluoromethyl)-phenyl]-2-pyrazolidine [briefly BW-755C, FEBS Lett. 110, 213–215, (1980)], 5,8,11,14-eicosatetraynoic acid [briefly, TYA, Prostaglandins 14, 21–38, (1977)], baicalein phosphate disodium [briefly, BPS, Taisha (Metabolism) 10, 730–739 (1973)], etc. The present inventors conducted a search for antiallergic substances and especially those substances which would inhibit the generation and release of SRS-A. As a result, it was found that a compound of the following general formula (I) causes a strong inhibition of generation and release of SRS-A and is useful as an antiallergic agent. This invention is based on the above finding.

The present invention provides a method for treatment of a mammal suffering from allergic diseases due to SRS-A, which comprises administering to said mammal an effective amount of a compound of the formula:

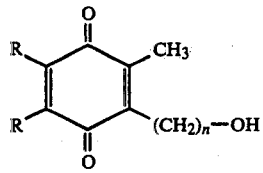

(I)

wherein R is methyl or methoxy, or the two R's taken together represent —CH=CH—CH=CH—; and n is an integer of from 4 to 22.

The present invention also provides a medicinal composition for the treatment of a mammal suffering from allergic disease due to SRS-A, which comprises, as an active ingredient, an effective amount of a compound of the formula (I) and a physiologically acceptable carrier, excipient or diluent therefor, as well as the use for a therapeutic agent of the compound (I) or the composition as defined above.

The compounds (I) generally, and particularly the compounds (I) in which R is methoxy, are excellent in the above-mentioned pharmacological properties, and the compounds (I) wherein n is 6 to 20 are particularly suited for the purposes of this invention.

The above-mentioned compound (I) may be exemplified by 2,3-dimethoxy-5-methyl-6-(4-hydroxybutyl)-1,4-benzoquinone, 2,3-dimethoxy-5-methyl-6-(6-hydroxyhexyl)-1,4-benzoquinone, 2,3-dimethoxy-5-methyl-6-(6-hydroxyhexyl)-1,4-benzoquinone, 2,3-dimethoxy-5-methyl-6-(9-hydroxynonyl)-1,4-benzoquinone, 2,3-dimethoxy-5-methyl-6-(10-hydroxydecyl)-1,4-benzoquinone, 2,3-dimethoxy-5-methyl-6-(11-hydroxyundecyl)-1,4-benzoquinone, 2,3-dimethoxy-5-methyl-6-(12-hydroxydodecyl)-1,4-benzoquinone, 2,3-dimethoxy-5-methyl-6-(13-hydroxytridecyl)-1,4-benzoquinone, 2,3-dimethoxy-5-methyl-6-(18-hydroxyoctadecyl)-1,4-benzoquinone, 2,3-dimethoxy-5-methyl-6-(20-hydroxyeicosyl)-1,4-benzoquinone, 2,3-dimethoxy-5-methyl-6-(22-hydroxydocosyl)-1,4-benzoquinone.

The compound (I) can be prepared by a per se known method, for example, the method described in U.S. Pat. No. 4,139,545 or an analogous method thereto, namely, by reacting a compound of the formula:

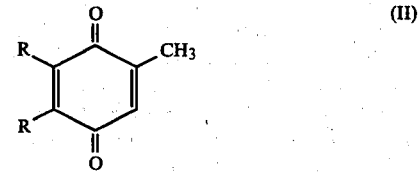

(II)

wherein R has the meaning given above with a compound of the formula:

(III)

wherein n has the meaning given above, to give a compound of the formula:

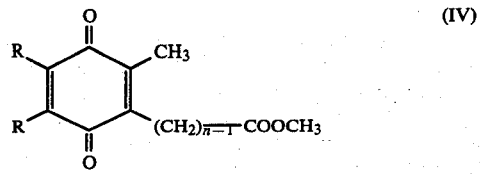

(IV)

wherein R and n have the meanings given above, and then reducing the compound (IV) by means of a reducing agent, for example, lithium aluminum hydride following oxidation with ferric chloride. The reaction of compound (II) with compound (III) is advantageously conducted in a suitable inert solvent such as, n-hexane, ligroine, toluene, xylene, acetic acid or propionic acid. The reaction temperature is advantageously in the range of about 80° C. to 100° C., and the reaction time is desirably in the range of about 0.5 to 3 hours. For reducing the compound (IV), any procedure may be taken so long as the carboxyl group may thereby be converted to an alcoholic hydroxyl group. As such procedures, there may be mentioned reduction by means of lithium aluminum hydride. Generally this reduction is advantageously conducted in the presence of such a suitable solvent as diethyl ether, tetrahydrofuran and dioxane.

The compound (I) strongly inhibits the generation and release of SRS-A in mammals (e.g. human being, mouse, rat, rabbit, dog and monkey), and it is used for alleviation or therapy of various allergic diseases due to SRS-A (e.g. bronchial asthma, allergic rhinitis, urticaria).

The compound (I) may be safely administered, orally or parenterally, as it is or advantageously as a pharmaceutical composition comprising an effective amount of the compound (I) and a physiologically acceptable carrier, excipient or diluent therefor, in the form of, for example, powder, granule, tablet, hard capsule, pill, ointment, soft capsule, dry syrup, suppository, aerosol, inhalant, injection or the like.

The composition for oral administration such as powder, granule, tablet, hard capsule, soft capsule and dry syrup may be prepared by a per se known conventional manner, and may comprise carriers, excipients or diluents conventionally used in the pharmaceutical art. For example, suitable carriers or excipients include lactose, starch, sugar, magnesium stearate, etc. As the excipients in the preparation of soft capsules, there may be used nontoxic, pharmaceutically acceptable oils and fats of animal, vegetable or mineral origin. The essential active ingredients are generally dissolved in these oils and fats before filling soft capsules therewith.

The compositions for parenteral administration may, for example, be injections, suppositories, aerosols and inhalant. The injectable preparations may be prepared in the form of solutions or suspensions. Since compounds (I) are soluble in oil but only sparingly soluble in water, injectable preparations in the form of aqueous solutions may be prepared by using solubilizing agents, if desired. As such solubilizing agents, there may be used nonionic surfactants that have adequate HLB values and are selected from among the nonionic surfactants generally used in the preparation of injectable solutions. The suppositories for rectal administration can be prepared by incorporating the compound (I) with a conventional suppository base. The aerosols and inhalant can also be prepared by a known conventional manner.

The composition of this invention contains a drug of dosage unit form. The drug of dosage unit form means a drug containing a daily dose of the compound (I) to be described hereinafter, or its multiples (up to 4 times), or its measures (down to 1/40), which is in the physically separate unit form suitable for administering as a medicine. Each dosage unit generally contains 0.3 mg to 100 mg of the compound (I). Among them, an injection ampoule preferably contains 0.3 mg to 30 mg, and each of the other forms preferably contains 5 mg to 100 mg of the compound (I).

The dosage of the compound (I) varies with the kinds of diseases, symptoms, administration routes or dosage forms, but, in case of parenteral administration such as injection, the daily dose as the compound (I) is about 0.3 mg to 100 mg (0.006 mg to 2 mg/kg), preferably 1 mg to 30 mg (0.02 mg to 0.6 mg/kg) for adult humans, and in case of oral administration, the daily dose is about 5 mg to 500 mg (0.1 mg to 10 mg/kg), preferably 10 mg to 300 mg (0.2 mg to 6 mg/kg) for adult humans.

In a test in rats (each group consisting of 10 rats), when the compounds of the invention were administered at a dose of 500 mg/kg once a day consecutively for 5 weeks, no abnormalities as compared with the control group were observed in any respect, namely in general condition, body weight, food consumption, urinalysis, general hematology, blood biochemistry, examination of liver for lipids, autopsy examination of organs, histopathology, enzymohistology, etc. These doses in rats are 50–5,000 times as much as the clinical doses mentioned above, and therefore it may be said that the compounds practically have no adverse effects from the clinical viewpoint.

EXPERIMENTAL EXAMPLE

The action of the antiallergic agent of this invention to inhibit the production of SRS-A was investigated by the method of Orange and Moore [J. Immunol. 116, 392 (1976)]. To the lung fragment of a guinea pig (Hartley strain, females and males, body weights 300 to 350 g) sensitized with egg albumin as the antigen, were simultaneously added the compound (I) and the antigen and the amount of SRS-A generated and released thereon was assayed by the method of Brocklehurst (J. of Physiology 151, 461–435, (1960)). The results are set forth in the Table. The compound (I) strongly inhibits the production and release of SRS-A at low concentrations.

TABLE

Inhibitory action on the generation and release of SRS-A

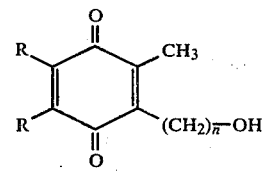

| Compound(*) | | Concentration | Inhibitory action |
|---|---|---|---|
| R | n | (M) | (%)(**) |
| H$_3$CO | 4 | 1 | 27.8 ± 11.9 |
|  |  | 10 | 64.2 ± 8.0 |
| H$_3$CO | 6 | 1 | 54.5 ± 9.2 |
| H$_3$CO | 10 | 1 | 66.0 ± 10.3 |
| H$_3$CO | 13 | 1 | 64.0 ± 3.5 |
| H$_3$CO | 18 | 1 | 43.0 ± 5.7 |
| H$_3$CO | 22 | 1 | 22.8 ± 5.1 |
|  |  | 10 | 75.5 ± 6.5 |
| H$_3$C | 10 | 10 | 38.4 ± 9.9 |
| BW-755C |  | 10 | 4.7 ± 3.7 |
|  |  | 100 | 15.3 ± 4.3 |
| TYA |  | 1 | 1.3 ± 1.2 |
|  |  | 10 | 56.9 ± 5.9 |
| BPS |  | 10 | 18.7 ± 6.6 |
|  |  | 100 | 50.8 ± 10.7 |

(*)The compound was added as a solution dissolved in ethanol or dimethyl sulfoxide.
(**)Percent inhibition of generation and release of SRS-A due to antigen-antibody interaction.

EXAMPLE 1

Capsules

| | |
|---|---|
| Compound of this invention (formula I wherein R = OCH$_3$, n = 10) | 30 mg |
| Microcrystalline cellulose | 30 mg |
| Lactose | 57 mg |
| Magnesium stearate | 3 mg |
| Total | 120 mg |

The above components are admixed and filled into gelatin capsules by the established pharmaceutical procedure.

EXAMPLE 2

Tablets

| | |
|---|---|
| Compound of this invention (formula I wherein R = OCH$_3$, n = 13) | 30 mg |
| Lactose | 44 mg |
| Starch | 10.6 mg |
| Starch (size) | 5 mg |
| Magnesium stearate | 0.4 mg |
| Carboxymethylcellulose-calcium | 20 mg |
| Total | 110 mg |

The above components were admixed and tableted by the established pharmaceutical procedure.

EXAMPLE 3

Soft elastic capsules

| | |
|---|---|
| Compound of this invention | |
| (formula I wherein R = OCH₃, n = 22) | 30 mg |
| Corn oil | 110 mg |
| Total | 140 mg |

The above components were made into a solution and processed into soft elastic capsules by the established pharmaceutical procedure.

What is claimed is:

1. A method for treatment of a mammal suffering from allergic disease due to SRS-A, which comprises administering to said mammal an effective amount of a compound of the formula:

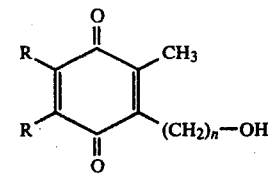

wherein R is methyl or methoxy, and n is an integer of from 4 to 22.

2. A method as claimed in claim 1, wherein the effective amount of the compound is 0.006 to 10 mg per kilogram of body weight of the mammal per day.

3. A method as claimed in claim 1, wherein n in the formula is an integer of from 6 to 20.

4. A method as claimed in claim 1, wherein the compound is 2,3-dimethoxy-5-methyl-6-(10-hydroxydecyl)-1,4-benzoquinone.

5. A method as claimed in claim 1, wherein the compound is 2,3-dimethoxy-5-methyl-6-(6-hydroxyhexyl)-1,4-benzoquinone.

6. A method as claimed in claim 1, wherein the compound is 2,3-dimethoxy-5-methyl-6-(13-hydroxytridecyl)-1,4-benzoquinone.

7. A method as claimed in claim 1, wherein the compound is 2,3-dimethoxy-5-methyl-6-(18-hydroxyoctadecyl)-1,4-benzoquinone.

* * * * *